United States Patent
Wessel (10) Patent No.: US 6,494,830 B1
(45) Date of Patent: Dec. 17, 2002

(54) HANDHELD CONTROLLER FOR MONITORING/USING MEDICAL PARAMETERS

(75) Inventor: Paul Wessel, Delano, MN (US)

(73) Assignee: Guidance Interactive Technologies, Inc., Delano, MN (US)

( * ) Notice: Subject to any disclaimer, the term of this patent is extended or adjusted under 35 U.S.C. 154(b) by 0 days.

(21) Appl. No.: 09/884,968

(22) Filed: Jun. 21, 2001

Related U.S. Application Data (60) Provisional application No. 60/213,422, filed on Jun. 22, 2000.

(51) Int. Cl.[7] .................................................. A61B 5/00
(52) U.S. Cl. ....................... 600/300; 273/459; 434/235; 600/365; 178/903
(58) Field of Search ................................. 600/300–301, 600/365, 347, 309–310, 316, 322; 128/903–904; 702/19, 104; 379/106.01, 106.02; 434/235–238, 262; 273/429, 440, 459, 148 B (56) References Cited

U.S. PATENT DOCUMENTS

| | | | |
|---|---|---|---|
| 5,134,391 A | | 7/1992 | Okada |
| 5,307,263 A | | 4/1994 | Brown |
| 5,507,288 A | * | 4/1996 | Böcker et al. ............... 600/300 |
| 5,678,571 A | | 10/1997 | Brown |
| 5,840,020 A | | 11/1998 | Heinonen et al. |
| 5,857,967 A | | 1/1999 | Frid et al. |
| 5,876,351 A | | 3/1999 | Rhode |
| 5,899,855 A | | 5/1999 | Brown |
| 5,913,310 A | | 6/1999 | Brown |
| 5,918,603 A | | 7/1999 | Brown |
| 5,960,403 A | | 9/1999 | Brown |
| 5,961,451 A | * | 10/1999 | Reber et al. ................. 600/322 |
| 6,295,506 B1 | * | 9/2001 | Heinonen et al. ............ 702/104 |
| 6,379,301 B1 | * | 4/2002 | Worthington et al. ........ 600/309 |

FOREIGN PATENT DOCUMENTS

WO  WO 00/78210 A1 * 12/2000 ............ A61B/5/00

* cited by examiner

Primary Examiner—Max Hindenburg
Assistant Examiner—Michael C Astorino (57) ABSTRACT

The Invention presents a system and method of combining a medical device, a medical testing procedure, in a combination of hardware and software that provide motivation and digital rewards through a hand held video game controller or other hand held computing device.

7 Claims, 8 Drawing Sheets

HANDHELD CONTROLLER FOR MONITORING/USING MEDICAL PARAMETERS

CROSS-REFERENCE TO RELATED APPLICATIONS

This application claims priority to U.S. Provisional Patent Application No. 60/213,422 filed on Jun. 22, 2000 which is incorporated herein by reference.

BACKGROUND OF THE INVENTION

Juvenile Diabetes strikes about 15,000 children every year under the age of 20. Currently, the United States has over 200,000 of these children that daily struggle with this disease. Contraction of diabetes requires the afflicted to frequently monitor blood glucose in order to avert long-term damage to their kidneys, eyes, and feet. However, there is no blood glucose testing devices currently available that provide or incorporate any motivation or reward mechanisms to encourage the individual to continue this testing regimen. Because the majority of the diabetic population is adults, most commercially available glucose testing meters are designed in such a fashion that is not user-friendly or socially acceptable to children. This causes children to shy away from blood glucose testing in a social setting. This anti-social aspect could expose them to episodes of hypoglycemia, hyperglycemia, and/or insulin shock.

Abstinence from regular blood glucose testing, for any reason, can have a devastating impact on the long-term wellness of the diabetic adolescent and contribute to significant increases of future health care costs. There have been many articles written and scientific studies conducted about incorporating motivational stimuli into medical testing procedures yet no significant improvements have been made to these devices. Many positive outcomes have been realized and the increased testing compliance has been achieved. (Lieberman, Debra—Health Education Video Games for Children and Adolescents: Theory, Design, and Research Findings)

Researchers in the field of diabetes are exploring technologies and methodologies to perform non-invasive glucose blood-level monitoring in Type I and Type II diabetics. Currently, there are two popular types of technology used in determining blood glucose levels that are found in the majority of home glucose monitoring devices. First, is the reagent type and the second is an enzyme/current differential device. The reagent strip or chemically reactant strip method requires placement of a small blood sample on a chemically treated test strip. A amount of glucose in the blood changes the color of the chemically treated test strip. A differential measurement is then taken from the test strip without a blood sample and compared to the color of the test strip once the blood has been placed on the strip and a finite testing period has been allowed to elapse. The enzyme/current differential method determines proper blood glucose by determining the amount current change that takes place when a glucose blood sample is placed on the test strip. An enzyme coating of the test strip directly affects the electrical resistance of the test strip. With both technologies proper glucose level is determined by comparison of either the color properties or the electrical current change in the test strip.

One of the most difficult challenges in the glucose testing device market has been to develop a glucose-testing device that does not require a small capillary blood sample. The "non-invasive" approach would become a huge commercial success because it would eliminate the element of pain associated with extracting a blood sample and increase the frequency of blood glucose testing.

It is public knowledge that one of the non-invasive approaches that could become commercially available is using a series of EKG/EEG readings, associated with a host of complex algorithms to determine blood glucose levels. It is not believed, however, that there are not any commercially available products incorporating such technologies and/or methodologies, although a commercially viable EKG/EEG glucose-monitoring device may soon become available. It is also believed that due to this research, other new products, incorporating other sensors might become available to detect epileptic seizures and asthma attacks.

SUMMARY OF THE INVENTION

The Invention presents a system and method of combining a medical device, a medical testing procedure, in a combination of hardware and software that provide motivation and digital rewards through a hand held video game controller or other hand held computing device.

In view of the potential commercial availability of these types of devices, the embodiments of the invention miniaturize and consolidate medical diagnostic electronic circuitry with additional software and hardware circuits that provide motivational elements before, during and after the diagnostic testing procedure. Such medical diagnostic electronic circuits are those that perform tests for blood glucose, high blood pressure, lipids, peak and flow, and oxygen saturation. All of the aforementioned circuits would be redesigned into a physical form that allows said medical circuits to be physically inserted into a socially acceptable hand-held microprocessor driven controller, such as a GAMEBOY® or HANDSPRING® Personal Desk Assistant.

After glucose data is converted and proper readings are displayed via the LCD on the invention and/or stored, a user of the device can select from a menu of different commands generated by the motivational hardware/software structure of the invention. Such games would be intended to educate and encourage more frequent participation in testing and maintaining proper glucose levels. The determined medical test results serve as a root motivation for the player to advance within, regress, complete, and/or be eliminated from the game or other form of entertainment provided by the device. The entertainment portion according to an embodiment of the invention may contain multiple games within a single cartridge or adapter module. Provisions are also being made to change games via the Internet. Daily, weekly, monthly, and yearly selection of historical values or other data can be user-defined and implemented through different hardware or software switches in the device. According to another aspect of the invention, the hardware/software stores these glucose values to an EEPROM that can be retrieved at a later date,

DETAILED DESCRIPTION OF THE PREFERRED EMBODIMENTS

In view of the potential commercial availability of these types of devices, embodiments of the present invention incorporate different glucose conversion techniques, reagent, enzyme electrical, and ECG/EEG, in operative combination with a preferably handheld microprocessor-driven controller. Such a controller includes an hand held video game controller, such as a GAMEBOY® controller, a personal digital assistant (more commonly referred to as a PDA), including those of a design similar to a PALM PILOT or HANDSPRING, and a cellular telephone.

Embodiments of the invention will now be described with more specific reference to the figures.

Figure 1:
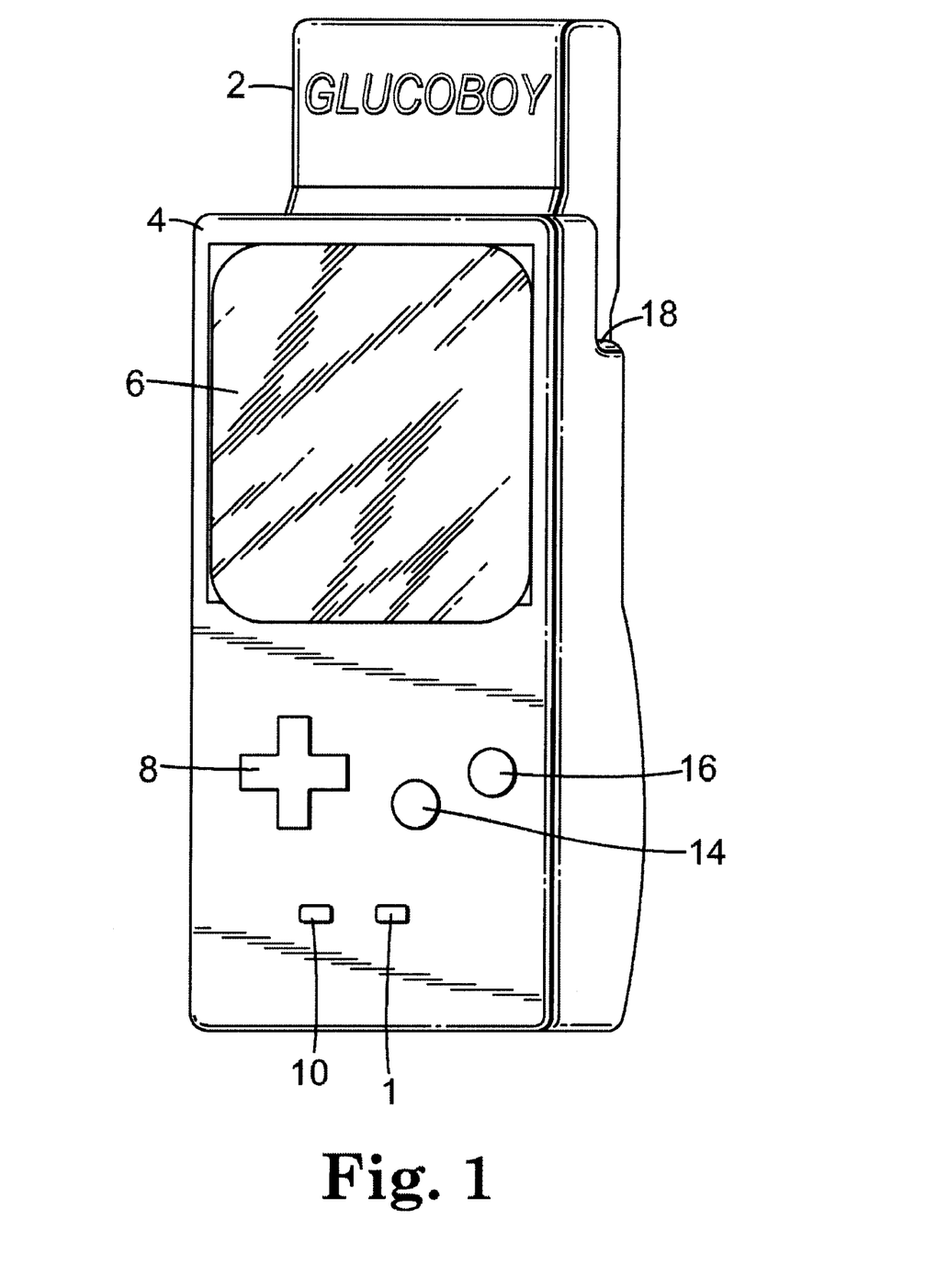
FIG. 1 illustrates the front view of the Invention inserted into a hand held video game controller according to an embodiment of the invention.

FIG. 1 Illustrates a hand held video gaming controller 4 that includes push buttons, 14,16,10,1 a primary display 6, directional controls 8, a software gaming cartridge interface 18 that is used to operate many commercially available software video gaming programs. FIG. 1 also shows how the Invention 2 is inserted into that hand held video gaming controller 4 utilizing the identical software gaming cartridge interface 18. A history of medical testing data is stored within the medical circuitry 30 of FIG. 3 that is found within the Invention 2. Depression of either push button, 14,16, located on the hand held video gaming controller 4, produces a primary electronic signal to the motivational hardware and software circuit combination 24 of FIG. 3. This event transmits a secondary electronic signal to the medical software and hardware circuit combination 30 of FIG. 3 through data communication line 28 of FIG. 3. This sequence of operation causes the glucose testing results, held within the medical software and hardware circuit combination 30 of FIG. 3, to be downloaded into a memory location within the motivational hardware and software circuit combination. This method of this data acquisition is further explained in the attached flowchart FIG. 5 although other means of data acquisition and transfer are contemplated.

Figure 2:
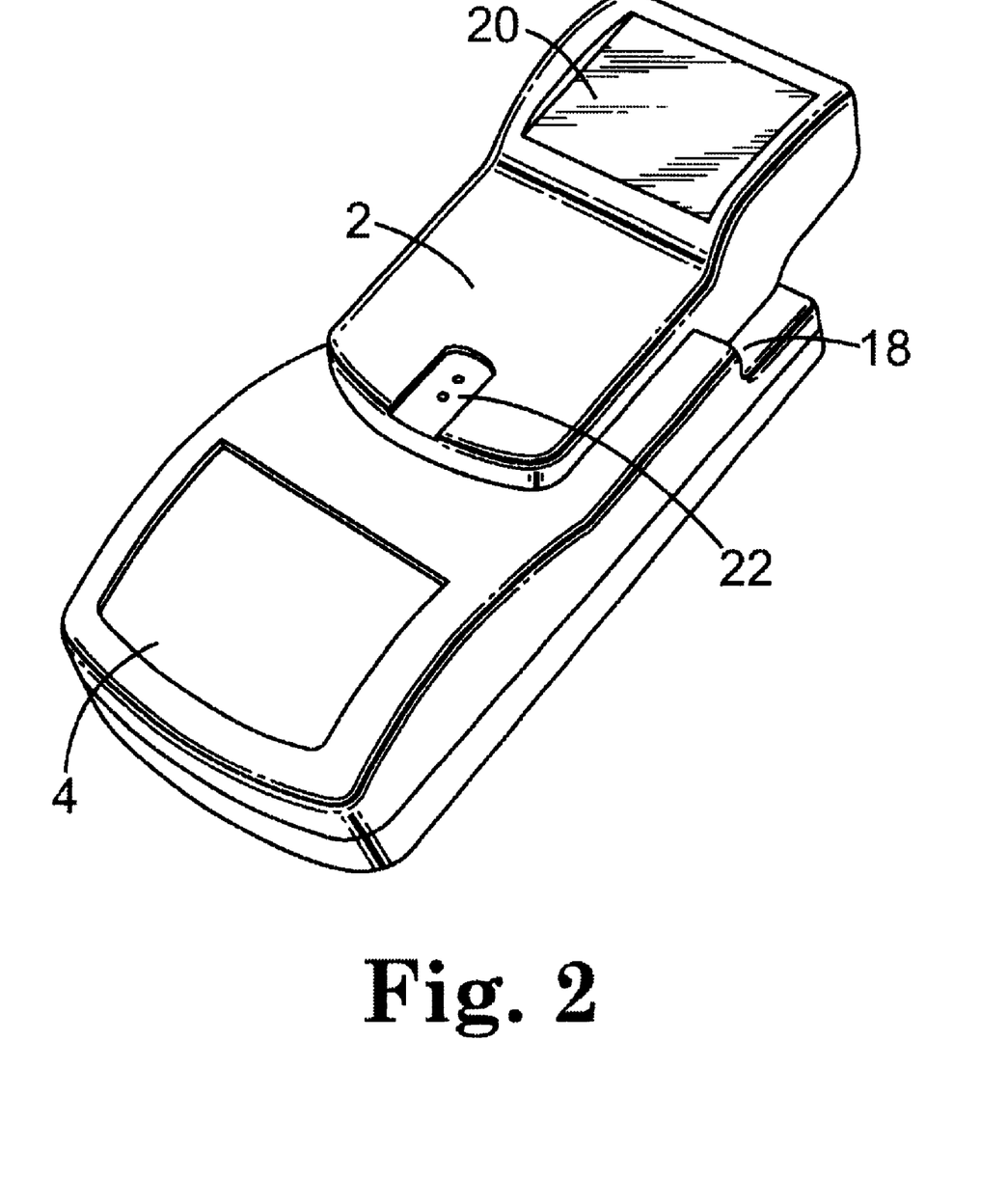
FIG. 2 illustrates the rear side of the Invention while inserted into a hand held video game controller according to an embodiment of the invention.

FIG. 2—illustrates a rear perspective of the Invention 2 inserted into a hand held video game controller. This particular illustration depicts the primary display panel 20 that operates independent of the hand held video gaming controller 6. A test strip insertion area 22 for reading a blood sample applied to a test strip is shown beneath the primary display means 20. Other axial locations of the primary display 20 and the test strip insertion point are contemplated.

Figure 3:
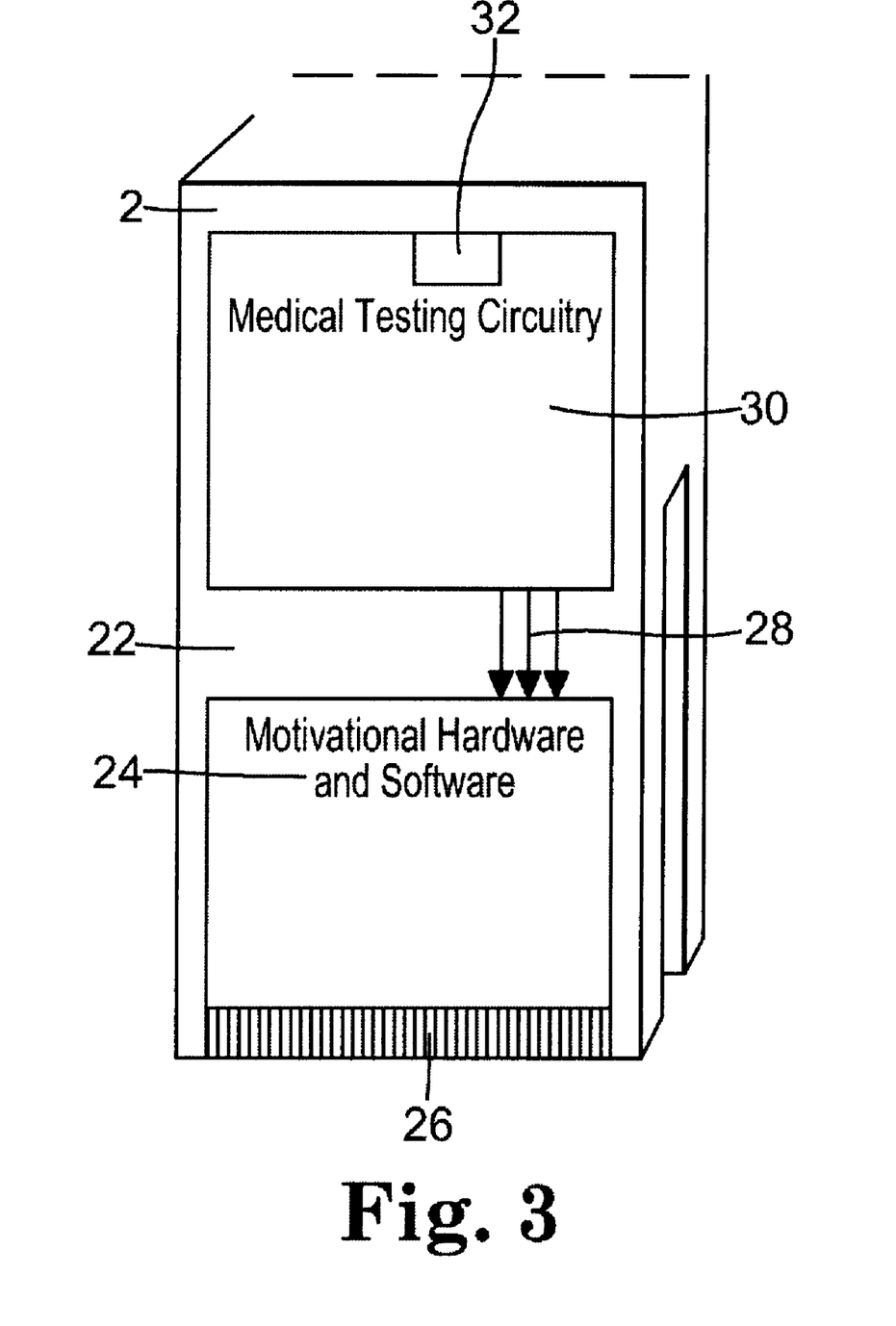
FIG. 3 illustrates the two electronic circuits contained within a single mechanical enclosure according to an embodiment of the invention.

FIG. 3—Illustrates the internal circuit design of the Invention 2 of FIG. 1 whereby two independent circuits exist, 30, 24 and are connected by a data communications line 28 all of which are contained within a single embodiment. The data communications line 28 is shown as a physical wired connection but other methods of data communication, such as optical, infrared, or wireless are contemplated. Another important feature of the Invention 2, is the motivational and software circuit combination 24 incorporates a specific hardware interface 26, that allows it to be inserted into the identical hardware interface 18 that receives and operates commercially available video gaming cartridges that are played on the hand held video game controller 4 of FIG. 1. It is contemplated that that these two independent circuits, 30,24 could be placed on a single circuit board layout and still operate independent of each other, reducing size and cost.

Figure 4:
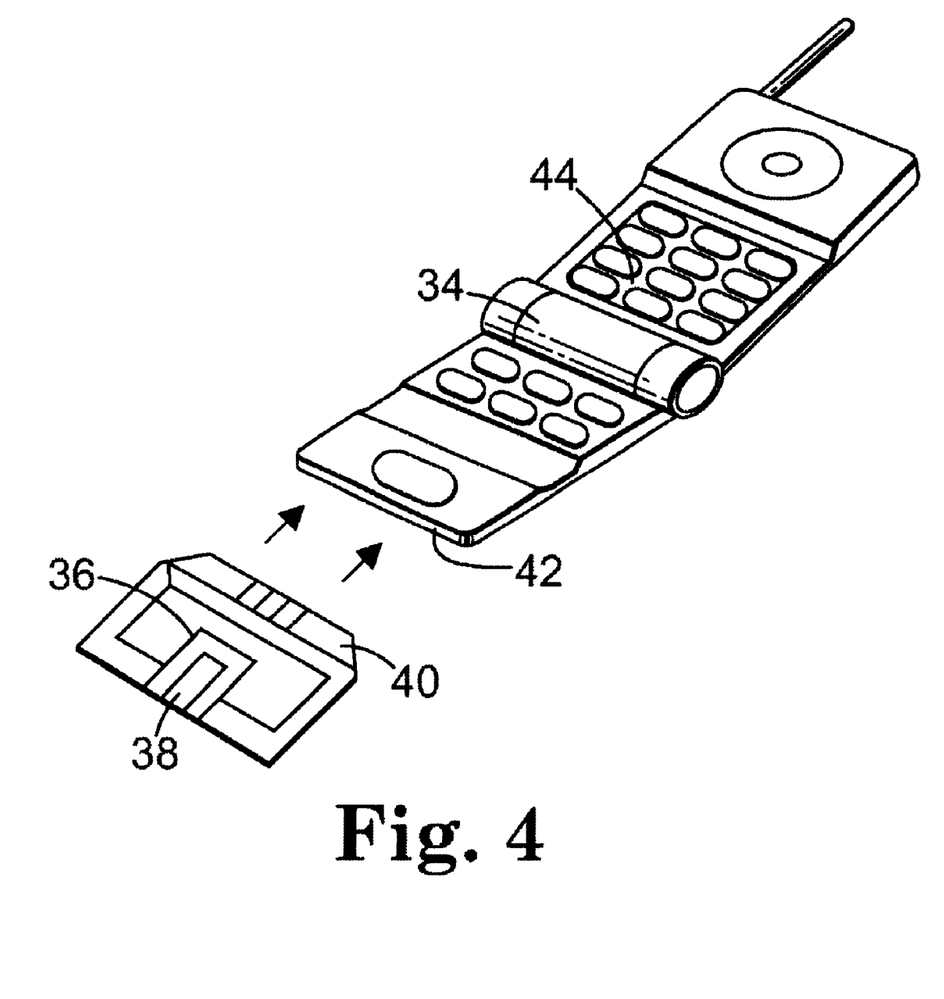
FIG. 4 illustrates a different version of the Invention that is inserted into a cellular telephone according to an embodiment of the invention.

The invention 2 of FIG. 1 can also be considered as a separate adapter 36 of FIG. 4 that is mechanically and electronically affixed to a hand held video game controller, cellular telephone and other portable computing devices. Glucose values, stored within the motivational hardware and software circuit combination 24 can be further transmitted to remote location, e.g. by using external communications capability of the hand held video game controller 4 of FIG. 1 or cellular telephone 44 of FIG. 4.

FIG. 4—Illustrates a different variation of the Invention using cellular telephone 34 and wireless cellular communications. While this variation of the Invention 34 is mechanically different, its internal electronics are identical to those found in FIG. 3, 30. This could be especially advantageous for people suffering from diabetes. Blood glucose data can be determined by the Invention 36 by analyzing a blood sample that has been placed on a test strip and inserted into the test Strip reception area 38. Once a test result has been determined, it is stored within the medical hardware and software circuit combination 30 of FIG. 3 contained within the Invention 36. This information can then be easily uploaded into a memory location of the cellular telephone 34 by depressing several preprogrammed buttons from the keypad 44 of the cellular telephone. At this point, the user transmits this glucose test data, via a preexisting cellular network, directly to a healthcare provider, independent data warehouse or assessment center, or other remote location. Health care providers and other can receive data more quickly and accurately to determine the proper treatment regimen. Reply communications to the user are also contemplated. Via a digital cellular network, the user can receive email, voice, or text messages from the healthcare provider or receive interactive motivational messages as to results of that data that was transmitted.

The commercial revenue potential for implementing this variation of the Invention 36 is enormous. If a telephone service provider would charge a minimal fee for each transmission of medical testing data, even for a small percentage of the diabetes market within the United States, the annual revenue realized would quickly exceeds multiple million of dollars.

Figure 5:
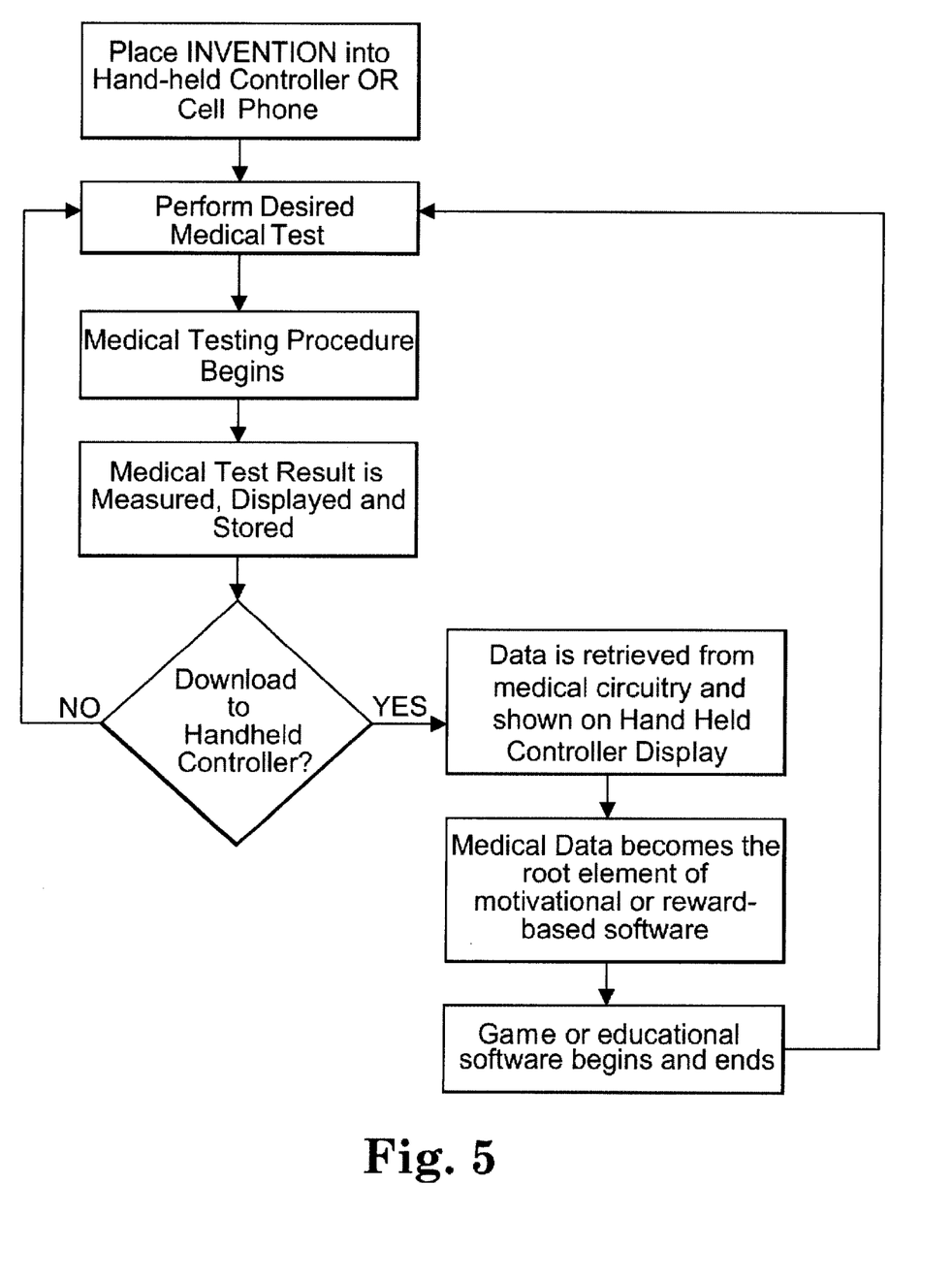
FIG. 5 is a flowchart according to an embodiment of the invention.

FIG. 5—illustrates the method of how the Invention 2 operates within a hand held video game controller or cellular telephone. The user first inserts the Invention 2 of FIG. 1 into the hand held controller 4 of FIG. 1 or cellular telephone 34 of FIG. 4, 60. Second, the user is prompted to conduct the medical test 62. Third, the user conducts the medical test 64 according to the proper medical procedures for conducting the test. When the medical hardware software combination 30 of FIG. 3 has completed the medical test procedure, the test results are displayed on the primary display means 20 of FIG. 2 on the Invention 2 of FIG. 1 and stored within a specific memory location of medical hardware software combination 30 of FIG. 3, 66.

After the medical test has been conducted, the Invention 2 of FIG. 1 is inserted into the hand held video game controller 4 of FIG. 1. A text message is displayed on the screen of the hand held video game controller 6 of FIG. 1 that prompts the user to initiate a download sequence of the test result 66 from the memory of the medical hardware and software circuit combination 30 of FIG. 3 into the memory of the motivational hardware and software circuit combination 24 of FIG. 3. When the user wants to perform this data download procedure 70, he depresses any of the hand held video controller push buttons, 16,8,10,1 of FIG. 1. This generates an electronic signal from the motivational hardware and software circuit combination 24 of FIG. 3 that requests the stored medical test data from the medical hardware and software circuit combination. This retrieved data 70 then becomes the root determinant for progression, regression, or elimination for receiving a reward or motivational software program 72. The user enters his choice of reward and begins game play until the game is over 74.

Figure 6:
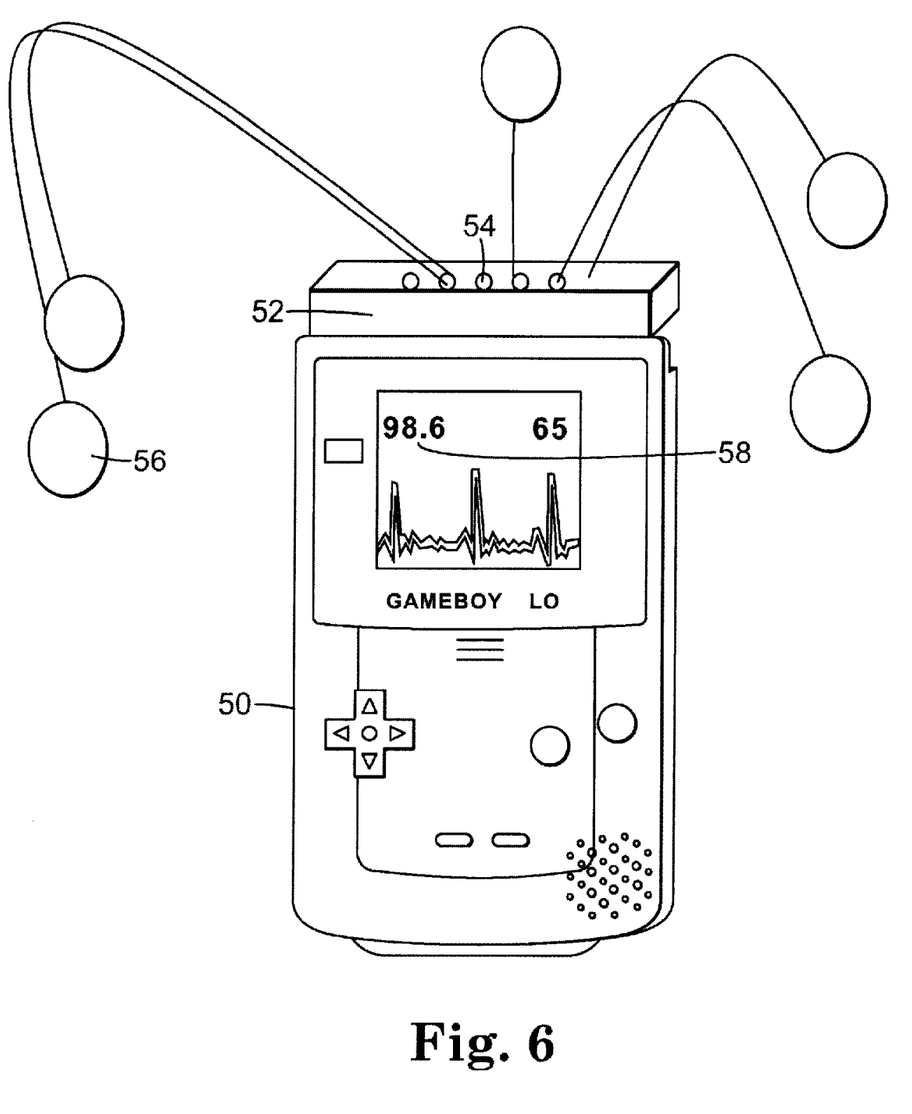
FIG. 6 illustrates another version of the invention that is used for medical entertainment and displays certain physiological information on the hand held video game controller according to an embodiment of the invention.

FIG. 6—illustrates another embodiment of the Invention 50. This is used for entertainment and educational purposes only. This "high-tech" medical kit is comprised of a GAMEBOY® or similar type device 4, in combination with a video gaming or program cartridge 52 that contains external sensor input insertion points 56, digital signal processing circuits 80, for interpreting data from a varied number of electronic sensors 56 that might be used to obtain different types of physiological information.

Figure 7:
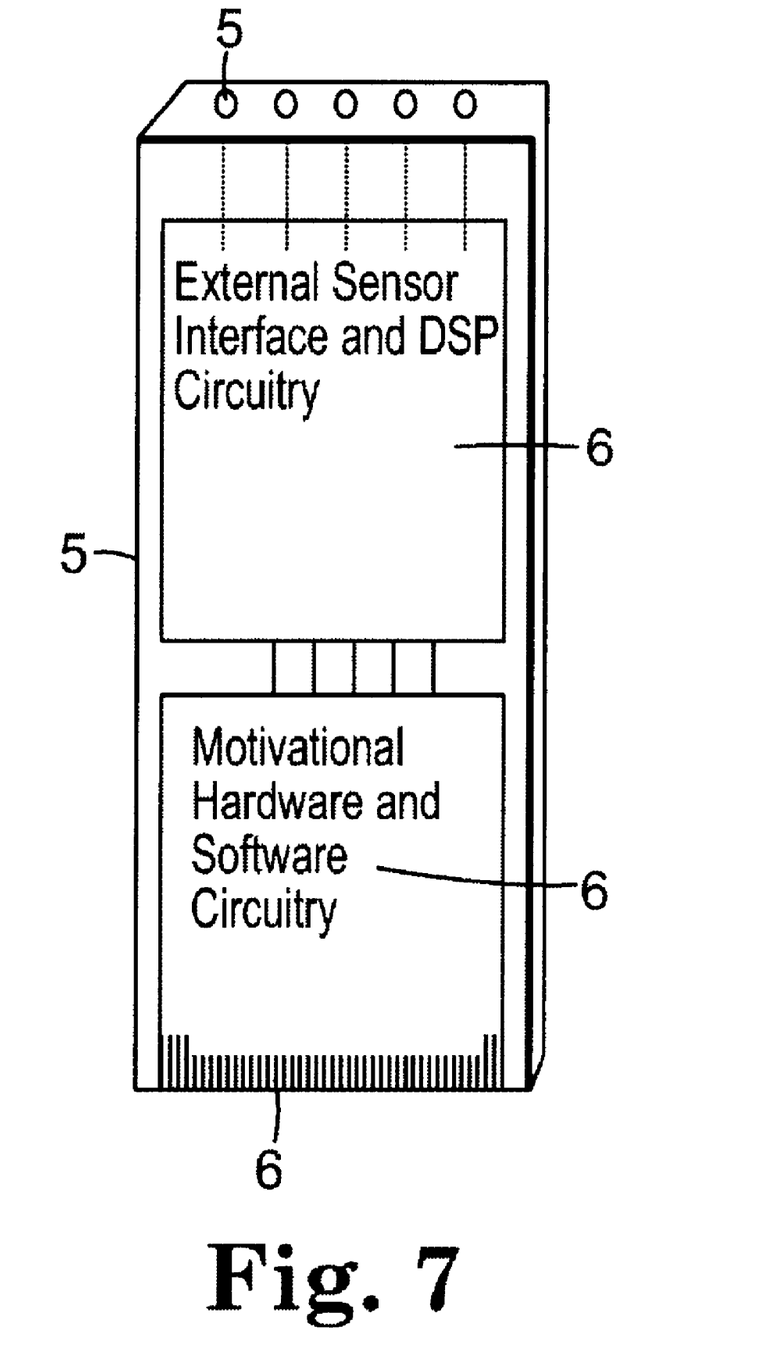
FIG. 7 illustrates a different version of the electronic circuit combination contained within a single mechanical enclosure according to an embodiment of the invention.

FIG. 7—This game cartridge increases interactive learning about different parts of the anatomy, either human or animal. Using the example of a temperature sensor, for example, a person playing "doctor" could obtain a temperature read-out 58 from a "patient" on the GAMEBOY device's or other device's LED or color display 6. The display is user configurable to a desired physiological output. The software then allows the operator to understand fundamentals contributing to the patient's temperature. After the current game or learning session is completed, an associated medical examination or quiz would allow the player to be promoted from game level to game level, e.g. from candy striper to LPN, if the parameters for passing the examination are met.

Different types of sensors and applications usable according to embodiments of the invention include: photo-electrics for sensing heart rate, blood sensing, height sensing; piezo-resistive for strength measurement, weight measurement, heartbeat detection, lung capacity measurement; pressure for measuring lung capacity, blood pressure, and pressure-based scalpel; mass air flow sensing for determining lung capacity; fiber optic sensors for measuring measurement or viewing the inner ear; thermocouple sensing for measuring body temperatures; carbon dioxide and oxygen sensors, moisture sensors for performing sweat analysis and moisture detection, glucose monitoring, as described herein, and ultrasonic sensors for profiling bone structure and height measurement.

According to more entertainment-oriented embodiments, hardware and software combinations are offered in different versions such as an EMT version, army medic version, veterinarian version, emergency room version, and others. Telephone modem, e-mail, internet access, and other communication modes already incorporated into the band held video game controller like a GAMEBOY or other off-the-shelf portable computing device enable remote teaching or grading from educational facilities or other remote locations. Thus, an effective learning tool for teachers and students is provided. Other, more detailed versions are contemplated for personal computers, video gaming consoles and other machines in addition to other hand held computing devices.

Figure 8:
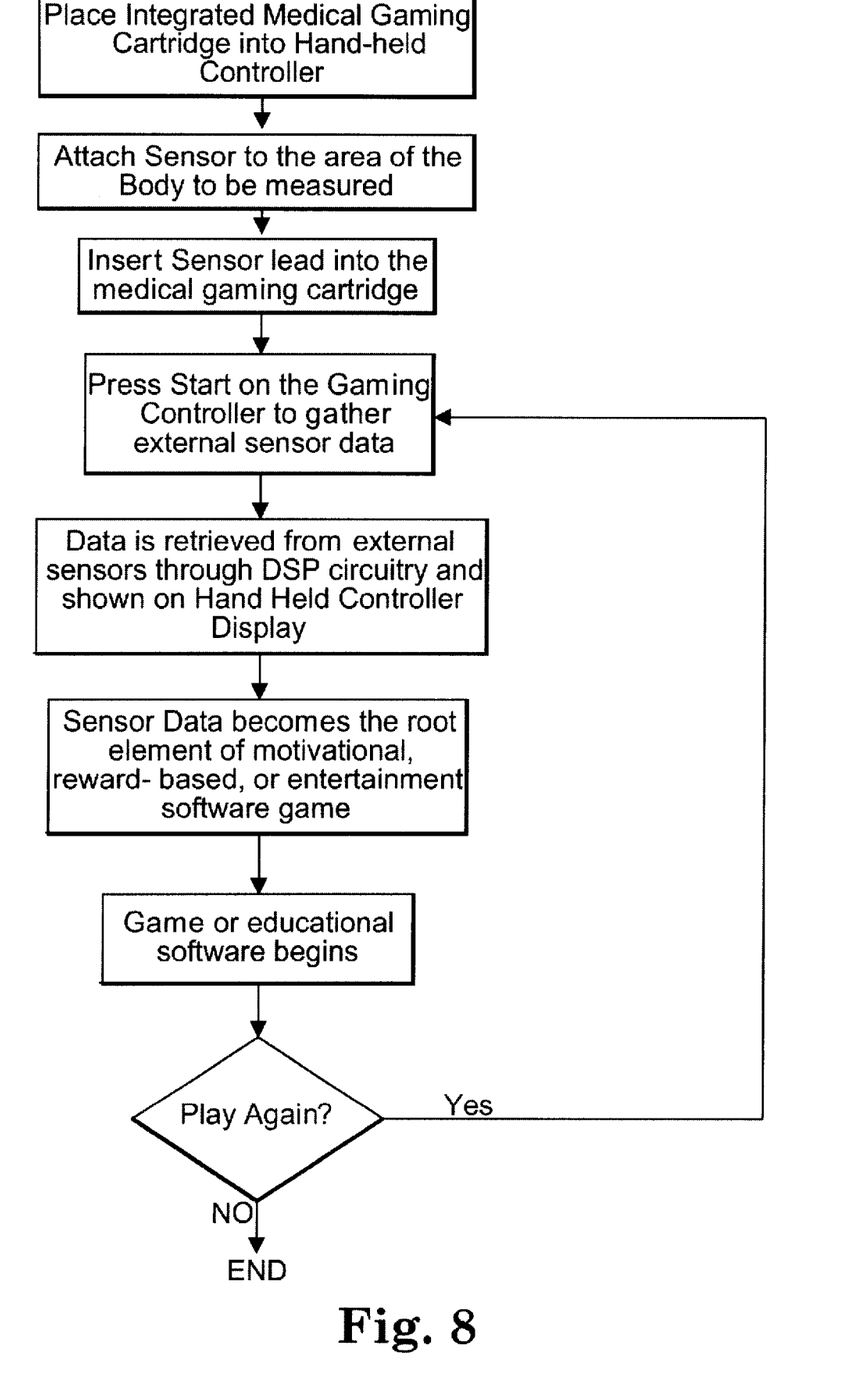
FIG. 8 is a flowchart according to an embodiment of the invention.

FIG. 8—Illustrates the method of operation for using the entertainment and educational version of the Invention 52 of FIG. 6. The user places the Invention 52 of FIG. 6 into the hand held video game controller to begin the gaming session 90. The user then selects and attaches the appropriate sensor to the part of the body that he wishes to acquire sensor data from 92. The user then places the sensor lead, power and data output signals to the sensor interface 54 of Invention 52. Once communication has been established between the sensor 56 of FIG. 6 and the Invention 52, the game begins 96. The gaming software prompts the user to acquire sensor data 98. Dependent upon the sensor's output capability, information in then displayed on the screen 58 of FIG. 6 of the hand held video controller 50 of FIG. 6, 98. Other display means, such as graphical, textual, or audio are contemplated.

While the invention has been described and illustrated with respect to particular embodiments, the invention is not to be considered limited to such embodiments. Many modifications and changes will be apparent to those of ordinary skill in the art. Devices other than GAMEBOY devices, PDA's, and the other off-the-shelf devices referenced herein are usable according to embodiments of the invention, for example. Other glucose monitoring devices or methods, such as analyzing a small blood sample for glucose concentration, can be used instead of EKG/EEG monitoring devices and methods, in connection with embodiments of the invention. Embodiments of the invention also can be used in connection with e.g. asthma and/or epileptic seizure detection devices and methods. Other variations will be apparent to those of ordinary skill.

The embodiments of the invention in which an exclusive property or privilege is claimed and defined as follows:

1. A medical monitoring system comprising:
   I. A module comprising:
      a. said module having a single mechanical housing that combines both medical diagnostic circuitry and supplemental video game circuitry for motivating or rewarding a user;
      b. a display on the housing for displaying medical test results;
      c. an interface that provides a physical connection from the housing into a hand held computing device;
      d. aperture on the housing wherein the aperture is adapted to allow insertion, retention, and analysis of a medical blood test strip for performing a blood glucose analysis;
      e. a power supply within the housing in the medical diagnostic circuit;
      f. wherein the supplemental video game circuitry comprises a means for receiving an electrical input or a plurality of inputs from the hand held video game controller;
      g. means for electronically sending medical testing results data from medical diagnostic circuitry to the supplemental video game circuitry;
      h. means for temporarily storing the medical test results in a memory location of the supplemental video game circuitry for determination of reward data to motivate a user of the system; and
      i. wherein said interface is used to send reward data from the to the hand held video game controller;
   II. A hand held computing device consisting of:
      a. A distinct operating system, power supply, and physical interface connection that allows for insertion and extraction and execution of different software programs of a particular mechanical interface;
b. An input device.

2. The system of claim 1 whereby the medical test results, is the determinant for progression, recession, completion or elimination for motivational stimuli.

3. The system of claim 1 whereby the stored medical test results, are the determinant for progression, recession, completion or elimination for motivational stimuli.

4. The system of claim 1 wherein an interface between the medical diagnostic circuitry and supplemental video game circuitry can be a hardwired or a wirelessly coupled interface.

5. The system of claim 1 wherein stored medical test results can be transmitted into a specific memory location within the supplemental video game circuitry; whereby the motivational test results can be transmitted by any external computing device the group comprising of:
desktop computer, laptop computer, PDA, cellular telephone or a hand held video game controller.

6. The system of claim 1 wherein the hand held computing device displays rewards and motivational information.

7. The system of claim 1 wherein the module display displays rewards and motivational information.

* * * * *